United States Patent [19]
Sutter et al.

[11] Patent Number: 6,102,951
[45] Date of Patent: Aug. 15, 2000

[54] MOUNTING SYSTEM FOR METALLIC SUPPORT SHELLS

[75] Inventors: Franz Sutter, Niederdorf; Roland P. Jakob, Môtier; Michael Adam, Marthalen; Roland Schoch, Baar, all of Switzerland

[73] Assignee: Sulzer Orthopaedie AG, Baar, Switzerland

[21] Appl. No.: 09/096,246

[22] Filed: Jun. 11, 1998

[30] Foreign Application Priority Data

Jun. 12, 1997 [EP] European Pat. Off. ............. 97810367

[51] Int. Cl.⁷ ........................... A61F 2/30; A61B 17/56
[52] U.S. Cl. .................... 623/18; 623/16; 606/72
[58] Field of Search .................... 623/18, 16, 11, 623/22, 18.11, 18.12, 16.11, 11.11; 606/72, 73; 411/187, 186, 185

[56] References Cited

U.S. PATENT DOCUMENTS

| | | | |
|---|---|---|---|
| 2,210,455 | 8/1940 | Hosking | 411/187 |
| 4,484,570 | 11/1984 | Sutter et al. | 128/92 D |
| 5,314,487 | 5/1994 | Schryver et al. | 623/22 |
| 5,397,360 | 3/1995 | Cohen et al. | 623/16 |
| 5,776,135 | 7/1998 | Errico et al. | 606/61 |
| 5,782,833 | 7/1998 | Haider | 606/61 |
| 5,785,524 | 7/1998 | Wolf | 433/173 |

FOREIGN PATENT DOCUMENTS 2060107  4/1981  United Kingdom ............. 411/187

*Primary Examiner*—Mickey Yu
*Assistant Examiner*—Alvin Stewart
*Attorney, Agent, or Firm*—Townsend and Townsend and Crew LLP

[57] ABSTRACT

With the invention a mounting system is shown for metallic support shells at implantable joints with pin-like metallic anchoring elements. The anchoring elements have a head which lies on a shoulder of the implant in the axial direction. Between the shoulder and the head there is a circular sealing edge. A contact pressure force is produced on the head by a contact pressure generating screw which is so great that a metallic seal is produced through plastic flow at the sealing edge which is liquid-tight and prevents the intrusion of abraded particles from the inner region of the support shell.

15 Claims, 4 Drawing Sheets

MOUNTING SYSTEM FOR METALLIC SUPPORT SHELLS

BACKGROUND OF THE INVENTION

The invention relates to a mounting system for metallic support shells at implantable joints with pin-like anchoring elements which can be anchored in the bone while passing through the support shell and which themselves have a head which lies on a shoulder of the implant in the axial direction of the pin-like anchoring element.

Support shells are used in artificial joints if the material of a bearing surface of the joint is in itself not sufficiently stiff in order to achieve a lasting anchorage in the bone, or if the bearing surface is to be made replaceable, or if the bearing material is not particularly well tolerated by the body. Typical support shells are tibia platforms and outer shells of artificial hip or shoulder joints. With respect to the primary anchoring of these support shells the surgeon is bound by the state of the bone at the intended mounting location and should therefore have a modular system available which permits different mounting means without alterations of the support shell.

Thus EP-B-0 499 475 shows a hip joint socket, the outer shell of which has a plurality of radial bores into which pins can be inserted and anchored. Other authors provide bone screws in order to produce a contact pressure force at the support shell in the direction of the screw axis. These systems have one disadvantage: They do not seal and therefore cannot prevent abraded matter passing through the bores and arriving at the parts of the bone lying behind them.

SUMMARY OF THE INVENTION

The object of the invention is to provide a modular system with different pin-like anchoring systems in which an effective sealing system seals the anchoring elements relative to the support shell.

This object is satisfied in that between the shoulder and the head there is a circular sealing edge which has a direct sealing action through plastic flowing at a predetermined axial force and prevents the intrusion of abrasion particles; and in that a contact pressure generating screw which produces the predetermined axial force at the head is attached to the implant behind the head.

The arrangement has the advantage that a metallic seal is produced through plastic flow at a sealing edge independently of an axial force from the pin-like anchoring element to the bone tissue, with manufacturing tolerances with respect to inaccuracies in shape and parallelism being compensated by the flow in order to provide a liquid-tight connection. This connection is independent of the type of the pin-like anchoring element. Bone screws inserted at an inclination or smooth positioning pins can likewise be used.

The dependent claims 2 to 10 claim advantageous further developments of the invention.

Depending on the type of the pin-like anchoring element, drilling jigs can be inserted which are restricted in their range of pivoting to an extent such that the latter corresponds to that range in which the pin-like anchoring elements can be inserted when the support shell has been set in place. The pin-like anchoring elements can have a cylindrical or a spherical head. The part protruding out of the support shell can be executed as a cylindrical pin, as a cylindrical pin with grooves, as the helix of a bone screw, as a tubule with projections and recesses, as a tubule with apertures, or as a tubule with an outer thread and apertures.

DESCRIPTION OF THE PREFERRED EMBODIMENTS

Figure 1:
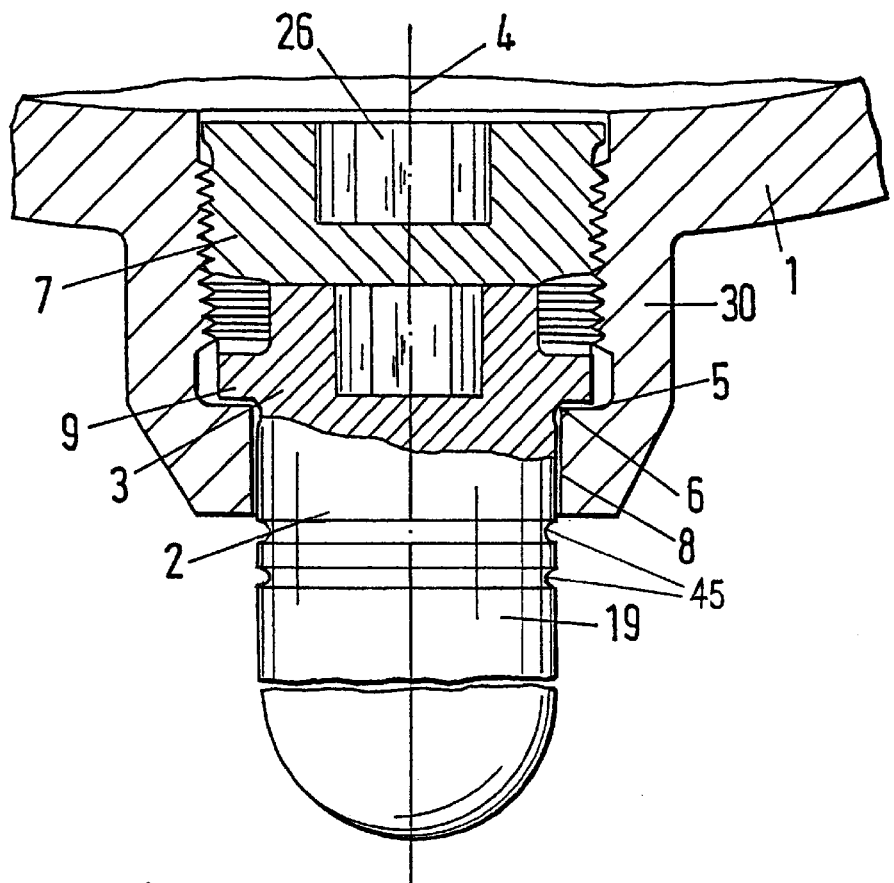
FIG. 1 is a schematic longitudinal section through a projection on a support shell with a cylindrical anchoring pin and with a sealing edge at this projection which acts on an inclined surface of the anchoring pin.

The figures show a mounting system for metallic support shells 1 at implantable joints with pin-like metallic anchoring elements 2. The anchoring elements have a head 3 which lies on a shoulder 5 of the implant in the axial direction 4. A circular sealing edge 6 is present between the shoulder and the head. In the embodiments shown in FIGS. 1, 3, 4 and 6, the edge of the shoulder 5 forms the circular sealing edge 6. In the embodiments shown in FIGS. 2 and 8, the circular sealing edge is formed on the anchoring member 2. A contact pressure force is produced on the head 3 by a contact pressure generating screw 7 which is so great that a metallic seal is produced through plastic flow at the sealing edge 6 which is liquid-tight and prevents an intrusion of abrasion particles from the inner region of the support shell 1.

In the example of FIG. 1, a support shell 1 is provided with a projection 30 which has a through-going bore 8 with a shoulder 5 following it along its longitudinal axis 4. The transition from the bore to the shoulder is executed as a sharp-edged circular sealing edge 6. An anchoring element 2 is executed as a cylindrical pin 19 which has a head 3 with a counter-shoulder 9, with the transition from the cylindrical part to the counter-shoulder 9 being executed as an inclined surface which rests on the sealing edge 6. The cylindrical pin 19 in FIG. 1 has transverse grooves 45.

The contact pressure required for a metallic seal is produced by a contact pressure generating screw 7 which is supported by a thread in the support shell 1 and which is screwed in in the direction towards the head 3 until a predetermined sealing force has been reached using a tool at a tool socket 26.

Figure 2:
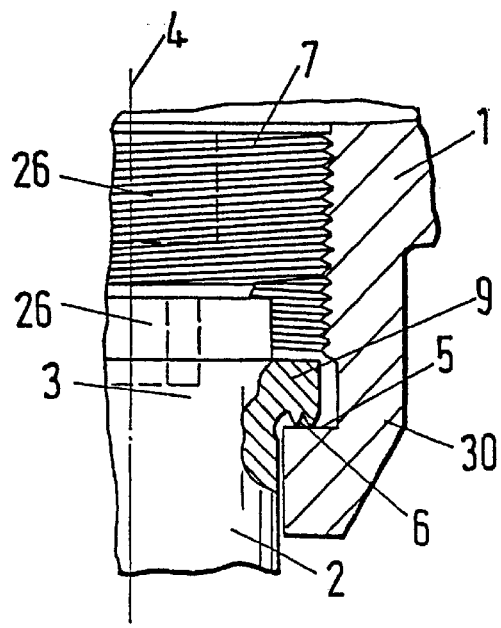
FIG. 2 is a schematic section as in FIG. 1 in which a double sealing surface is attached to the head of the anchoring pin and acts on a shoulder on the projection.
Figure 8:
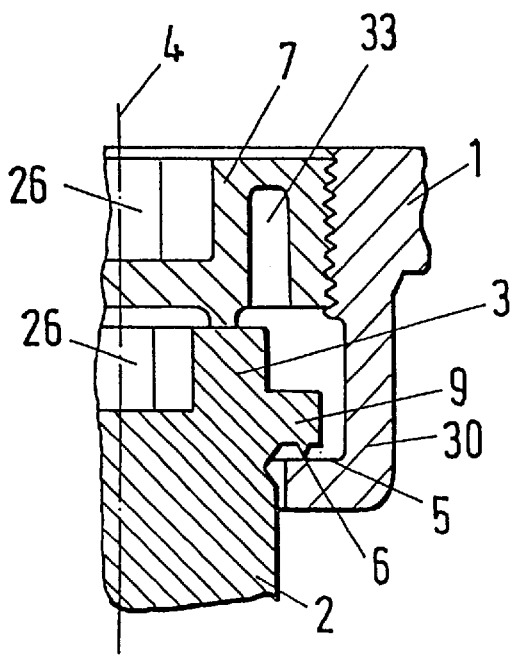
FIG. 8 is the schematic arrangement of FIG. 2 with an elastic bias force of the screw connection.

In the example of FIG. 2 two sealing edges 6 are provided on the counter-shoulder 9 of the head 3 and lie on the shoulder 5 of the projection 30. A screw which corresponds to the contact pressure generating screw 7 in FIG. 1 and is supported in the same thread as in FIG. 1 in the support shell provides the required sealing force. The geometry of the sealing edges 6 is matched in this arrangement to the plastic behavior of the material of the support shell 1 and the anchoring pin 2. The wall strength of the projection 30 can be intentionally kept small in this situation in order to achieve an increased spring action in the screw connection under the sealing force. A minimum force is thereby maintained after the plastic deformation and consolidation has taken place. In FIG. 8, for the same arrangement with one sealing edge 6, the projection 30 with its supporting cross-section is kept slender and a groove 33 is produced a the screw 7 in order to increase the spring action.

Figure 3:
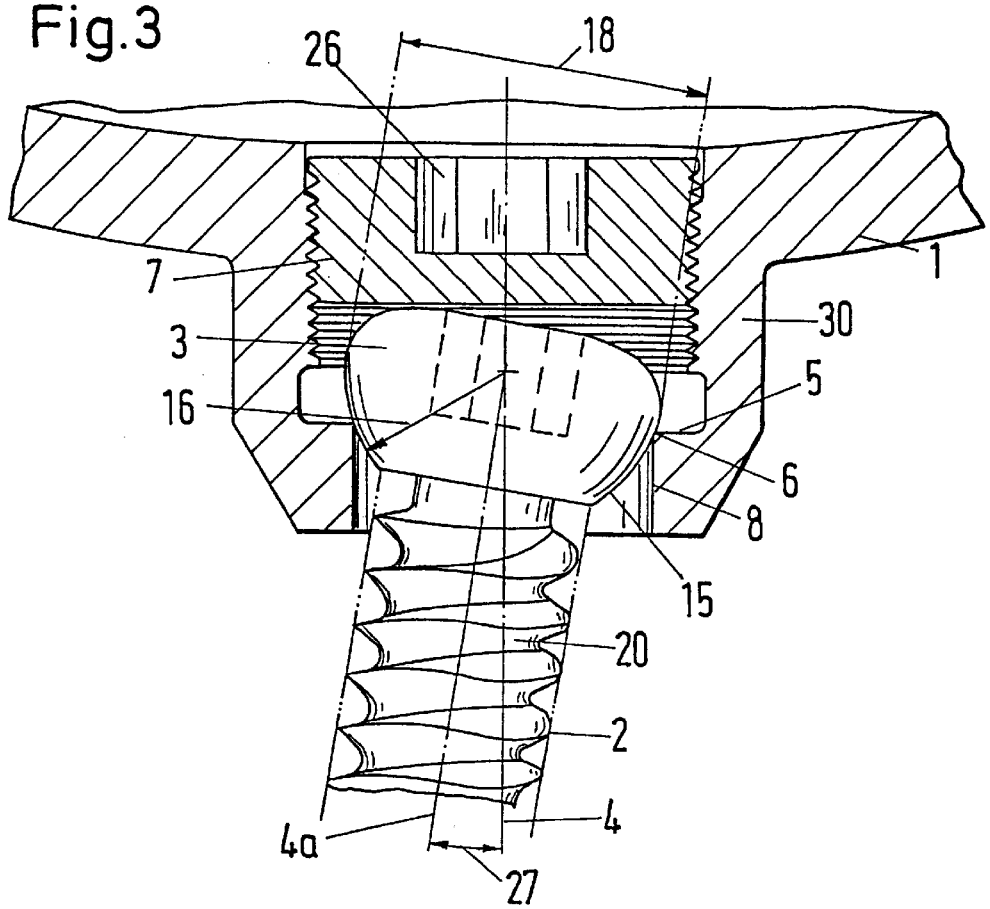
FIG. 3 is a schematic longitudinal section through a projection on a support shell with a bone screw which is clamped sealingly at its head.
Figure 6:
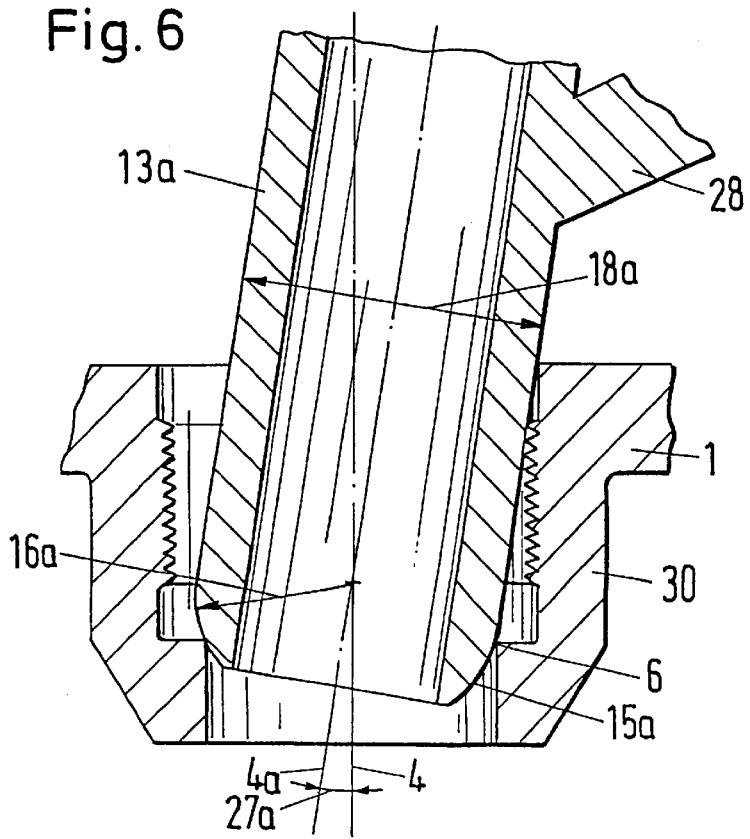
FIG. 6 is a schematic longitudinal section through a support shell with a drilling jig for an arrangement in accordance with FIG. 3.

In the example of FIG. 3 a bone screw 20 which has a head 3 with a spherical support surface 15 and a radius 16 lies on the sealing edge 6 of a projection 30 and centers itself there. The screw axis 4a is pivoted away from the longitudinal axis 4 of the projection 30 into an inclined position 27. The required sealing force is produced by the contact pressure generating screw 7, which is secured via a thread in the support shell 1. The tension is produced by a wrench which engages in a tool socket 26. In this situation the inclined position 27 is chosen in such a manner that the head 3 with its diameter 18 can be moved into and out of the threaded bore of the projection 30. In order not to exceed this inclined position 27 when the support shell 1 is inserted, a drilling jig 13a is shown in FIG. 6 which has a generally spherical surface 15a with a radius 16a and a cylindrical outer surface with a diameter 18a which corresponds to the diameter 18 of the screw head 3. The drilling jig 13a is set in place using a holder arm 28 and pivoted into a desired position. The inner diameter of the drilling jig is matched in this situation to the intended use of the anchoring element 2 and corresponds for example to the outer diameter of a cylindrical pin or to the core hole diameter for a bone screw.

Figure 5:
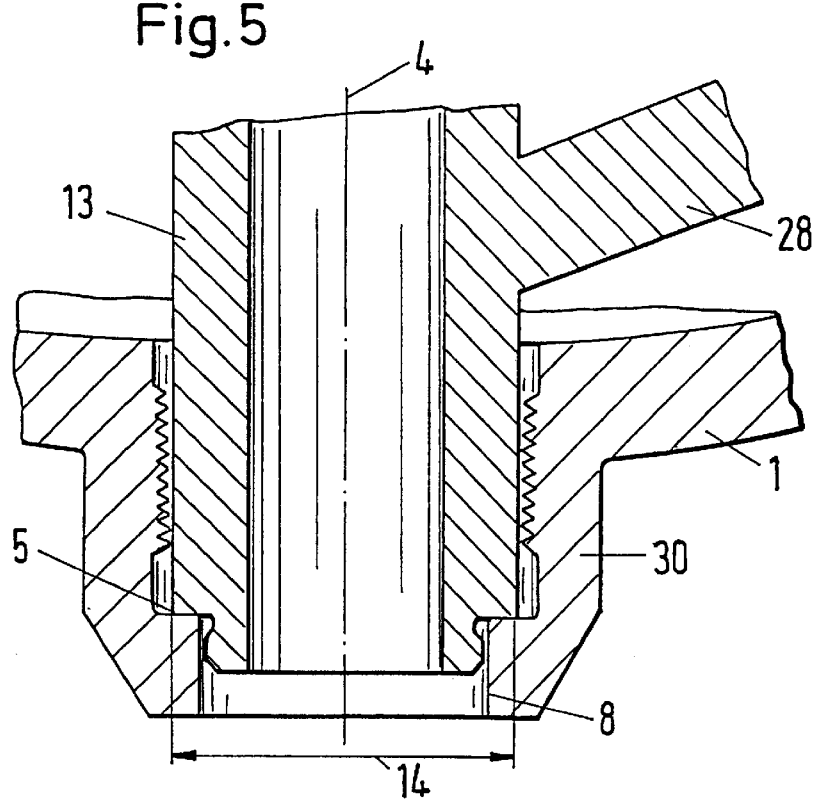
FIG. 5 is a schematic longitudinal section through a support shell with a drilling jig for an arrangement in accordance with FIGS. 1, 2, 4.

In contrast to this, the drilling jig 13 in FIG. 5 is supported on the shoulder 5 of the projection 30 and centers itself in the through-going bore 8 or in the threaded bore of the projection 30. With it, bores are possible in the direction of the longitudinal axis 4. A holder arm 28 enables the application and holding during the boring.

Figure 4:
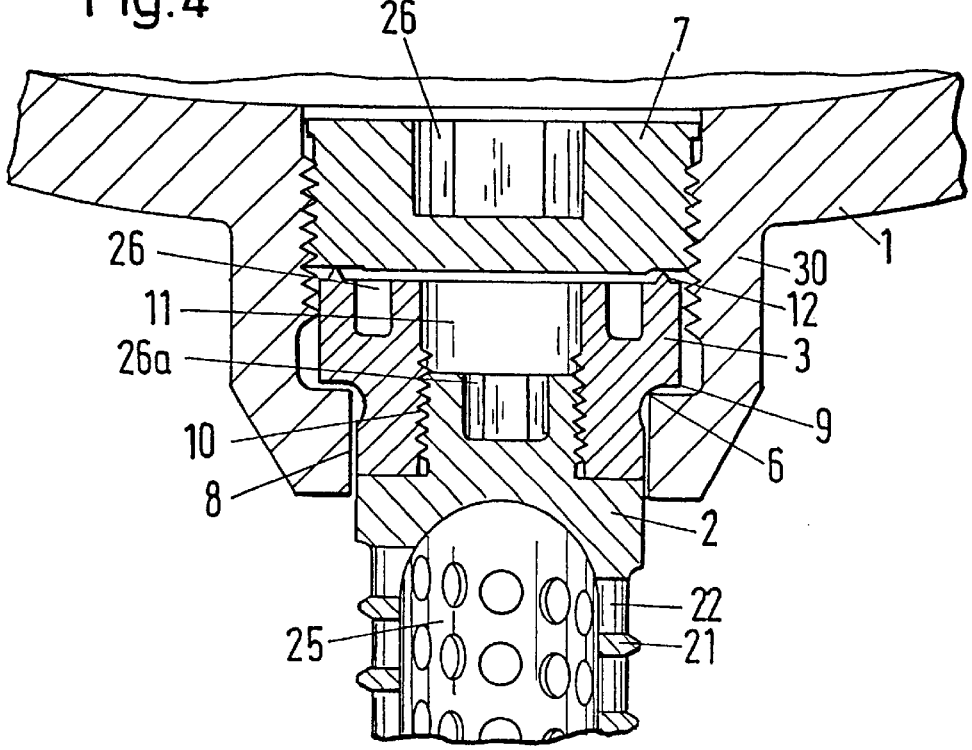
FIG. 4 is a schematic longitudinal section through a projection on a support shell with a bone screw which is hollow and has a removable head.

In the example of FIG. 4 the head 3 of the anchoring element 2 can be unscrewed. This enables the head 3 and the support shell 1 to be separated from an anchoring element 2 which has grown into the bone. A hollow bone screw with an outer thread 21 is shown in the form of a tubule 25 with apertures 22 which are intended to encourage the ingrowth of the bone tissue. The head 3 has an aperture 11 and blind sockets 26 for a rotary wrench (not shown here) which is hollow in order to be able to counter the torque acting when the head 3 is being released with a counter-torque applied by a second wrench inserted through the aperture 11 and engaging the tool socket 26a of the pin part 2. Due to the aperture 11 there is a second metallic seal in the form of a circular sealing edge 12 between the contact pressure generating screw 7 and the head 3.

Figure 7:
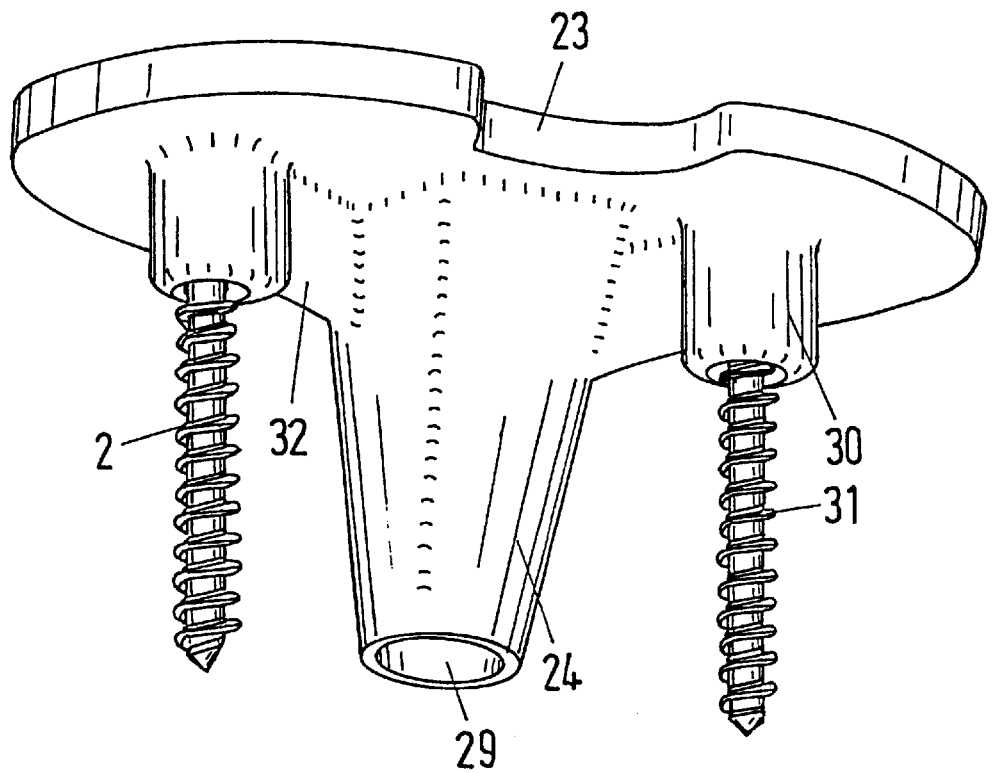
FIG. 7 is a schematic view of a support shell in the form of a tibia platform with two projections and bone screws anchored in each of them.

In FIG. 7 a tibia platform 23 is provided with a central spigot 24 and a bore 29 for shafts of different lengths. Reinforcement ribs 32 lead to projections 30 from which bone screws 31 project which can be anchored at the projections 30 with a metallic seal in accordance with the preceding examples.

The examples shown here can also be used in principle as mounting systems for metallic bone plates in traumatology since the metallic seal produced can transmit large forces in regard to the transmission of bending torques from a plate-like element to pin-like elements anchored in the bone. This property, which makes the connection insensitive to bending moments in regard to the tightness of the seal, is necessarily also a good anchorage between a bone plate and a pin-like element such as, for example, a bone screw. An embodiment shown by FIGS. 3 and 6 can be used especially well in operation techniques in which a plate reinforcing a bone is pushed beneath the muscles and is connected to the bone at its ends by bone screws. The plastic deformation in the metallic seal likewise produces a form fit for a better transmission of the forces.

What is claimed is:

1. A metal implant for bone joints, the implant comprising:

a metallic support shell having at least one hole and a shoulder around each hole, the shoulder being disposed on a bearing side; and a bearing mountable in the support shell, the bearing including at least one pin-like anchoring element configured to be introduced partially through the at least one hole and fixed in the metallic support shell from the bearing side, the pin-like anchoring element including a head disposed on the bearing side, the pin-like anchoring element contacting the shoulder at a circular metal sealing edge formed on the shoulder, the circular sealing edge being plastically deformable for forming a metal sealing between the pin-like anchoring element and the shoulder, the bearing including at least one contact pressure generating screw, the screw seated in the metallic support shell behind and abutting the head of the corresponding pin-like anchoring element for applying a sufficient force on the head to produce plastic flow of the metal sealing edge to form the metal sealing between the pin-like anchoring element and the corresponding shoulder of the metallic support shell, wherein the pin-like anchoring element includes a projecting part projecting through the corresponding hole of the metallic support shell.

2. A metal implant according to claim 1 wherein the contact pressure generating screw is seated in the metallic support shell for applying a force in an axial direction along an axis of the corresponding pin-like anchoring element.

3. A metal implant according to claim 1 wherein the contact pressure generating screw is seated in the metallic support shell for applying a force on the head of the corresponding pin-like anchoring element to produce plastic flow along an annular surface of the metal sealing edge to form the metal sealing between the pin-like anchoring element and the corresponding shoulder of the metallic support shell.

4. A metal implant according to claim 1 wherein the head of the pin-like anchoring element is spherical.

5. A metal implant according to claim 4 wherein the shoulder of the metallic support shell is disposed perpendicular to an axis of the corresponding pin-like anchoring element to form the circular sealing edge at the corresponding hole for contacting the spherical head of the pin-like anchoring element to form the metal sealing therebetween.

6. A metal implant according to claim 1 wherein the head of the pin-like anchoring element comprises a straight, ring-shaped counter-shoulder with at least one protruding sealing edge.

7. A metal implant according to claim 6 wherein the head of the pin-like anchoring element is detachably fastenable to the pin-like anchoring element by a releasable screw connection.

8. A metal implant according to claim 7 wherein the releasable head includes a central aperture for a tool and an upper circular sealing edge for sealing against the corresponding contact pressure generating screw.

9. A metal implant according to claim 1 wherein the projecting part comprises a cylindrical pin.

10. A metal implant according to claim 1 wherein the projecting part comprises a cylindrical pin with longitudinal grooves.

11. A metal implant according to claim 1 wherein the projecting part comprises a cylindrical pin with transverse grooves.

12. A metal implant according to claim 1 wherein the projecting part comprises a spiral thread of a bone screw.

13. A metal implant according to claim 1 wherein the projecting part comprises a tubule with projections and recesses.

14. A metal implant according to claim 1 wherein the projecting part comprises a tubule with apertures.

15. A metal implant according to claim 1 wherein the projecting part comprises a tubule with an outer thread and apertures.

* * * * *